United States Patent [19]

Alexander

[11] Patent Number: 5,221,776
[45] Date of Patent: Jun. 22, 1993

[54] SELECTIVE ISOMERIZATION OF OLEFINIC HYDROCARBONS

[75] Inventor: Bruce D. Alexander, Villa Park, Ill.

[73] Assignee: Amoco Corporation, Chicago, Ill.

[21] Appl. No.: 881,094

[22] Filed: May 11, 1992

[51] Int. Cl.$^5$ .............................................. C07C 5/27
[52] U.S. Cl. .................................... 585/671; 502/202
[58] Field of Search ................. 585/664, 666, 671; 502/202

[56] References Cited

U.S. PATENT DOCUMENTS

| | | | |
|---|---|---|---|
| 4,433,190 | 2/1984 | Sikkenga et al. | 585/660 |
| 4,499,326 | 2/1985 | Melquist | 585/664 |
| 4,503,282 | 3/1985 | Sikkenga | 585/671 |
| 4,777,310 | 10/1988 | Sikkenga et al. | 585/671 |

*Primary Examiner*—Anthony McFarlane
*Attorney, Agent, or Firm*—Thomas A. Yassen; Richard A. Kretchmer; Frank J. Sroka

[57] ABSTRACT

A process is provided for isomerizing an olefinic hydrocarbon feedstock and producing an olefinic isomerate product, wherein the feedstock comprises at least 10 weight percent of an olefinic hydrocarbon having 5 carbon atoms, comprising contacting the feedstock at isomerization conditions with an isomerization catalyst, the isomerization catalyst comprising from about 0.01 weight percent to about 50 weight percent borosilicate and from about 20 weight percent to about 99.99 weight percent of silica.

19 Claims, No Drawings

SELECTIVE ISOMERIZATION OF OLEFINIC HYDROCARBONS

BACKGROUND OF THE INVENTION

This invention relates to a process for selectively isomerizing olefinic hydrocarbons. More particularly, this invention relates to a process for selectively isomerizing olefinic hydrocarbons, such as normal amylene, utilizing a catalyst comprising low to medium concentrations of borosilicate with a binder comprising silica.

Oxygenates have been part of the United States gasoline strategy since the late 1970s. With the Clean Air Act Amendments of 1990, the demand for oxygenates are expected to increase even further. For example, starting in the winter months of 1992, gasoline containing 2.7 weight percent oxygen will have to be provided to approximately 40 metropolitan areas that have failed to meet carbon monoxide pollution standards. It is expected that in the near future, between 30 and 60 percent of the United States gasoline pool may be required to contain oxygenates. Current oxygenate production capacity is insufficient for meeting these requirements.

The most commonly used oxygenates today are methanol, ethanol, and methyl tertiary butyl ether (MTBE). Although methanol and ethanol have high blending octanes, problems with toxicity, water miscibility, high Reid Vapor Pressure (RVP), high nitrogen oxide emissions, lower fuel efficiency, and cost have dampened industry enthusiasm for these components. Partially as a result of the above, MTBE has become particularly attractive.

Homologues of MTBE such as ethyl tertiary butyl ether (ETBE) and methyl tertiary amyl ether (TAME) are also gaining industry acceptance. Moreover, commercial activity with respect to ETBE and TAME is expected to increase relative to MTBE, in view of the recent Environmental Protection Agency decision to reduce the RVP requirements for gasolines well below 9 psia, the blending RVP of MTBE.

Oxygenate production is not only limited by oxygenate plant capacity but by feedstock availability. MTBE and ETBE both utilize isobutylene as a feedstock. Isobutylene is generally supplied to an MTBE or ETBE facility in a petroleum refinery, from a fluid catalytic cracking unit (FCC), a fluidized or delayed coker, or from downstream paraffin dehydrogenation and isomerization facilities. The availability of hydrocarbons having 4 carbons is limited by constraints such as, but not limited to, crude properties, FCC catalyst properties, FCC operating conditions, and coking conditions, etc. The chemical mix of $C_4$ paraffins, olefins, and aromatics as well as the particular mix of iso-olefins to normal olefins are similarly constrained.

Once lower cost alternatives for expanding isobutylene availability have been exhausted, refiners are being faced with the decision of locating additional feed sources or erecting downstream facilities such as dehydrogenation and isomerization units, to convert normal butanes to isobutylene. Such facilities, which were not in commercial demand prior to such recent legislation, are particularly expensive to erect. Therefore, some refiners have opted for the production of TAME to provide incremental oxygenate supply, in view of problems associated with limited isobutylene availability and reduced gasoline RVP requirements. TAME utilizes isoamylene as a feedstock. However, isoamylene supply is subject to many of the same availability constraints as isobutylene.

Thus, there exists a great need in the petroleum industry for a method of increasing oxygenate production capacity. An obstacle to fulfilling this need is the limited availability of isoamylene feedstocks, necessary for the production of TAME.

Processes for isomerizing alkenes, and particularly normal butylene, are generally known in the art. The products of alkene isomerization have been used to provide reactants for polymerization, alkylation, and disproportionation reactions in addition to MTBE production.

U.S. Pat. No. 4,038,337 to Manara et al. discloses a process for the skeletal isomerization of alkenes utilizing a catalyst comprising alumina that has been treated with minor amounts of silica.

U.S. Pat. No. 4,548,913 discloses a process for the skeletal isomerization of alkenes utilizing a catalyst generally comprising zeolites at silicon to aluminum molar ratios of 300:1 to 5000:1.

The use of borosilicate-containing catalysts for oligomerization, isomerization, and aromatization has also been taught in the art.

U.S. Pat. No. 4,777,310 to Sikkenga discloses a process for selective gas-phase equilibration of olefins having 3 carbon atoms or more using a catalyst comprising a borosilicate molecular sieve and an inorganic matrix. An objective of the process is the maximization of total butylene and t-amylene production and minimization of aromatics. Process objectives are achieved by maintaining a particularly specified partial pressure of monoolefin feed and short catalyst and oil contact times.

U.S. Pat. No. 4,503,282 to Sikkenga discloses a process for converting substantially linear alkenes such as n-butene, to isomerized products using a catalyst comprising greater than 50 weight percent of a borosilicate molecular sieve with an inert binder. An objective of the process is to provide iso-butylene feedstocks for subsequent processing steps such as polymerization and oxidation.

U.S. Pat. No. 4,499,325 to Klotz et al. discloses a process for converting alkenes to oligomerized, aromatized, or isomerized products using a borosilicate catalyst composition. The process provides for a method to convert linear butenes to a mixture containing isobutylene, a method to dimerize the isobutylene using the borosilicate catalyst composition, and a method to convert the butenes to aromatics.

U.S. Pat. No. 4,499,326 to Melquist discloses a process for the isomerization of normal butene to isobutylene using a borosilicate catalyst composition and low reaction temperatures. An objective of the process is to provide a process that produces 2-butene from 1-butene for feedstock to an alkylation process so as to produce a higher octane alkylate product.

A problem attendant to such processes is that under field or commercial process conditions, such catalysts generally require periodic regeneration to maintain catalytic activity and selectivity. Upon experiencing regeneration conditions, which can include exposure to high temperatures and steam formed from the combustion of coke, such catalysts can experience substantial losses in isomer yield.

It has been found that under simulated regeneration conditions, typical borosilicate-containing catalysts, such as those described hereabove, can undergo a substantial loss in i-Amylene selectivity when utilized for n-Amylene isomerization. It has also been found that utilizing reduced amounts of crystalline borosilicate molecular sieve (less than 50 weight percent) combined with a silica binder, provides substantially improved i-Amylene yield performance, under commercial conditions, than borosilicate-containing catalysts having larger proportions of the crystalline borosilicate molecular sieve or borosilicate-containing catalysts comprising inorganic oxide binders other than silica.

It has also been found that the catalyst described herein, comprising reduced concentrations of crystalline borosilicate molecular sieve with a silica binder, provides even better performance when utilized under high reaction temperatures (between about 500° F. and 1200° F.) at a particularly targeted n-Amylene-containing feedstock space velocity (WHSV) of between about 4 hr$^{-1}$ and about 32/hr$^{-1}$. Lower space velocities generally result in i-Amylene selectivity losses that outpace the gains in n-Amylene conversion, resulting in lower i-Amylene yields. Higher space velocities result in losses in n-Amylene conversion that outpace the gains in i-Amylene selectivity, resulting in lower i-Amylene yields.

For purposes of the present invention, normal amylene conversion (n-Amylene Conv.), isoamylene selectivity (i-Amylene Sel.), and isoamylene yield (i-Amylene Yield) shall have the following meanings and be calculated by weight and in accordance with the following models:

$$\text{n-Amylene Conv.} = \frac{\Sigma\text{n-Amylene(feed)} - \Sigma\text{n-Amylene(product)}}{\Sigma\text{n-Amylene(feed)}}$$

$$\text{i-Amylene Sel.} = \frac{\Sigma\text{i-Amylene(product)} - \Sigma\text{i-Amylene(feed)}}{\Sigma\text{n-Amylene(feed)} - \Sigma\text{n-Amylene(product)}}$$

$$\text{i-Amylene Yield} = \frac{(\text{i-Amylene Sel.}) \times (\text{n-Amylene Conv.})}{100}$$

It is therefore an object of the present invention to provide a process that cost-effectively increases oxygenate production capability by increasing i-Amylene feedstock availability.

It is another object of the present invention to provide a process that can be operated reliably and effectively under conditions wherein the catalyst undergoes periodic regeneration.

It is another object of the present invention to provide a process that can easily accommodate a stand alone operating facility or incorporation with existing process units.

It is yet another object of the present invention to provide a process that can operate effectively in the presence of or without hydrogen.

Other objects appear herein.

SUMMARY OF THE INVENTION

The above objects can be achieved by providing a process for isomerizing an olefinic hydrocarbon feedstock and producing an olefinic isomerate product, wherein the feedstock comprises at least 10 weight percent of an olefinic hydrocarbon having 5 carbon atoms, comprising contacting the feedstock at isomerization conditions with an isomerization catalyst, the isomerization catalyst comprising from about 0.01 weight percent to about 50 weight percent borosilicate and from about 20 weight percent to about 99.99 weight percent of silica.

In another embodiment, the above objects can be achieved by providing a process for isomerizing an olefinic hydrocarbon feedstock and producing an olefinic isomerate product, wherein the feedstock comprises at least 25 weight percent of an olefinic hydrocarbon having 5 carbon atoms, comprising contacting the feedstock at isomerization conditions comprising a reaction temperature ranging from about 500° F. to about 1000° F., a reaction pressure ranging from about 0 psig to about 200 psig, and a feedstock WHSV ranging from about 4 hr$^{-1}$ to about 32 hr$^{-1}$, with an isomerization catalyst comprising from about 0.01 weight percent to about 30 weight percent borosilicate and from about 20 weight percent to about 99.99 weight percent of silica.

The process of the present invention cost-effectively increases oxygenate production capability by increasing i-Amylene feedstock availability. The present invention increases the volume of i-Amylenes by increasing the proportion of i-Amylenes to total Amylenes derived from facilities such as fluid cracking units, fluidized or delayed cokers, and dehydrogenation facilities. The i-Amylenes can be subsequently converted to TAME.

The process of the present invention can be operated reliably and effectively under conditions wherein the catalyst undergoes periodic regeneration. The catalyst utilized in the present invention is particularly hydrothermally stable and maintains superior i-Amylene yield performance under scenarios wherein the catalyst is exposed to conditions encountered in conventional regeneration systems.

The process of the present invention can operate effectively in the presence of or without hydrogen. Although operation of the present process in the presence of hydrogen reduces catalyst deactivation rates and the magnitude of regeneration required, the process can be effectively operated without hydrogen. Hydrogen supply facilities which generally require compression equipment, hydrogen separation systems, and sophisticated metallurgy can substantially reduce the cost effectiveness of the process.

The process of the present invention can accommodate a stand-alone operating facility or incorporation with existing process units. The present invention generally requires a feedstock preheat system, a reaction system, and regeneration facilities. Such facilities can be added to the tail end of a fluid catalytic cracking unit, the feed or product recovery sections of a TAME facility, the feed or product recovery sections of a dehydrogenation unit, or to any one or more of several refinery facilities wherein advantages, such as access to waste heat, hydrogen, feed or product systems, or operating personnel can be obtained.

BRIEF DESCRIPTION OF THE INVENTION

The hydrocarbon feedstock suitable for use with the present invention generally comprises substantially linear olefins or substantially linear alkenes including normal olefins containing from about 4 to about 10 carbon atoms, preferably from about 4 to about 8 carbon atoms, and more preferably from about 4 to about 6 carbon atoms for best results. In particular, the preferred feedstock comprises at least 10 percent by weight olefinic hydrocarbon having 5 carbon atoms, preferably at least 25 percent, and more preferably at least 50 percent, for best results. The group of olefinic hydrocarbon having 5 carbon atoms, for purpose of the present invention, will be referred to as the amylenes.

The hydrocarbon feedstock suitable for use with the present invention and comprising a substantial portion of amylenes will generally include hydrocarbon components such as, but not limited to, 1-pentene, cis-2-pentene, trans-2-pentene, 3-methyl-t-butene, 2 methyl-1-butene, 2-methyl-2-butene, and pentadiene. Non-amylene olefins including butenes such as 1-butene, cis-2-butene, trans-2-butene, and isobutylene can often be present in the feedstock but are not preferred. Similarly, non-olefinic components can also be present, including components such as normal and isobutane and normal and isopentane. The typical feedstock will generally comprise a mix of amylenes comprising a substantial portion of both normal amylenes and isoamylenes.

The hydrocarbon feedstock generally encountered in conventional petroleum refineries can vary widely in boiling range and chemical mix. The catalyst used in the process of the present invention is particularly tolerant to many forms of contamination. It is preferred, however, that the feedstock contain less than 10 percent by weight hydrocarbon having 7 carbon atoms, preferably less than 5 percent by weight, and more preferably less than 1 percent by weight for best results. The presence of heavier hydrocarbons in the feedstock can result in quicker catalyst deactivation and increase catalyst regeneration requirements.

The source of olefinic hydrocarbon feedstock components can include, but is not limited to, a fluid catalytic cracking unit, a fluidized or delayed coking unit, catalytic hydrocracking units, and/or naphtha dehydrogenation units. Olefinic hydrocarbons are generally produced from catalytic or thermal reactions and are not as commonly found, in high concentrations, in most petroleum crudes directly.

The olefinic hydrocarbon feedstock components can also be accumulated from recovery processes downstream of etherification processes such as TAME, MTBE, and ETBE facilities. In such processes, the ether product along with other unreacted components is directed to downstream processing steps for recovery of the ether component and redirecting of the remaining stream to other processing steps or product blending. Such processing steps can be manipulated to include recovery of feedstocks suitable for use in the process of the present invention. For example, TAME product from a TAME production process, along with unreacted isoamylene, normal amylene, and other components can be directed to a separation step for recovering and concentrating normal amylene. The normal amylene from such recovery steps can also be directed to the process of the present invention.

The process of the present invention comprises a catalyst having a crystalline borosilicate molecular sieve and an inorganic oxide support.

Crystalline borosilicate molecular sieves of the AMS type are preferred and have the following composition in terms of mole ratios of oxides:

$$0.9 \pm 0.2\ M_{2/n}O:B_2O_3:ySiO_2:zH_2O$$

wherein M is at least one cation having a valence of n, y ranges from about 4 to about 600, and z ranges from 0 to about 160, and provide an X-ray diffraction pattern comprising the following X-ray lines and assigned strengths:

| d-Spacing (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

For ease of reporting X-ray diffraction results, relative intensities (relative peak heights) were arbitrarily assigned the following values:

| Relative Peak Height | Assigned Strength |
|---|---|
| less than 10 | VW (very weak) |
| 10-19 | W (weak) |
| 20-39 | M (medium) |
| 40-70 | MS (medium strong) |
| greater than 70 | VS (very strong) |

The preferred borosilicate molecular sieve, by virtue of its superior stability and selectivity, is the AMS-1B type which is in the sodium form as synthesized. The original cation in the AMS-1B crystalline borosilicate molecular sieve, which usually is sodium ion, can be replaced all or in part by ion exchange with other cations including other metal ions and their amino complexes, alkylammonium ions, hydrogen ions, and mixtures thereof. Preferred replacing cations are those which render the crystalline borosilicate molecular sieve catalytically active, particularly for hydrocarbon conversion. Suitable catalytically active ions include hydrogen, metal ions of Groups IB, IIA, IIB, IIIA, VIB, and VIII, and ions of manganese, vanadium, chromium, uranium, and rare earth elements. The preferred form of AMS-1B is the hydrogen form, HAMS-1B, which can be prepared by ammonium exchange followed by calcination. Further details with respect to these crystalline borosilicate molecular sieves can be found in commonly assigned U.S. Pat. No. 4,269,813 to Klotz, which is herein incorporated by reference.

The AMS-1B borosilicate molecular sieve useful in this invention can be prepared by crystallizing an aqueous mixture of cation sources, an oxide of boron, an oxide of silicon, and an organic template compound, at a controlled pH.

Typically, the mole ratios of the various reactants can be varied to produce the crystalline borosilicate molecular sieve of this invention. Specifically, the mole ratios of the initial reactant concentrations are indicated below:

| | Broad | Preferred | Most Preferred |
|---|---|---|---|
| $SiO_2/B_2O_3$ | 5-400 | 10-150 | 10-80 |
| $R_2O^+/[R_2O^+ + M_{2/n}O]$ | 0.1-1.0 | 0.2-0.97 | 0.3-0.97 |
| $OH^-/SiO_2$ | 0.01-11 | 0.1-2 | 0.1-1 | wherein R is an organic compound and M is a least one cation having a valence n, such as an alkali metal or an alkaline earth metal cation. By regulation of the quantity of boron (represented as $B_2O_3$) in the reaction mixture, it is possible to vary the $SiO_2$ molar ratio in the final product.

More specifically, the material useful in the present invention is prepared by mixing a cation source compound, a boron oxide source, and an organic template compound in water (preferably distilled or deionized). The order of addition is generally not critical although a typical procedure is to dissolve sodium hydroxide and boric acid in water and then add the template compound. Generally, after adjusting the pH, the silicon oxide compound is added, with intensive mixing, such as that performed in a Waring blender. After the pH is checked and adjusted if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and more preferably between about 10.8 and about 11.2 for best results.

Examples of oxides of silicon useful in this invention include silicic acid, sodium silicate, tetraalkyl silicates, and Ludox, a stabilized polymer of silicic acid manufactured by E. I. DuPont de Nemours & Co. The silica source is preferably a low sodium content silica source containing less than 2,000 ppm sodium and more preferably less than 1000 ppm sodium, such as Ludox HS-40 which contains about 40 wt % $SiO_2$ and 0.08 wt % $Na_2O$ or Nalco 2327 which has similar specifications. The oxide of boron source is generally boric acid although equivalent species can be used such as sodium borate and other boron-containing compounds.

Cations useful in formation of AMS-1B include alkali metal and alkaline earth metal cations such as sodium, potassium, lithium, calcium, and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation with an organic base such as ethylenediamine.

Organic templates useful in preparing AMS-1B crystalline borosilicate molecular sieves include alkylammonium cations or precursors thereof such as tetraalkylammonium compounds. A useful organic template is tetra-n-propylammonium bromide. Diamines, such as hexamethylenediamine, can also be used.

It is noted that the preferable amount of alkylammonium template compound used in the instant preparation method is substantially less than that required to produce AMS-1B conventionally using an alkali metal cation base.

The crystalline borosilicate molecular sieve prepared by the instant method typically contains at least 9,000 ppm boron and less than about 100 ppm sodium and is designated as HAMS-1B-3. The HAMS-1B-3 crystalline borosilicate molecular sieve has a higher boron content and a lower sodium content than crystalline borosilicates formed using conventional techniques.

In a more detailed description of a typical preparation of the catalyst used in the process of the present invention, suitable quantities of sodium hydroxide and boric acid ($H_3BO_3$) are dissolved in distilled or deionized water followed by addition of the organic template. The pH may be adjusted between about $11.0\pm0.2$ using a compatible base or acid such as sodium bisulfate or sodium hydroxide. After sufficient quantities of silicic acid polymer (Ludox HS-40) are added with intensive mixing, the pH can again be checked and adjusted to a range of from about $11.0\pm0.2$. The resulting slurry is transferred to a closed crystallization vessel and reacted usually at a pressure of at least the vapor pressure of water for a time sufficient to permit crystallization. This time period generally ranges from about 6 hours to about 20 days, typically from about 1 day to about 10 days, and preferably extends from about 5 days to about 7 days. The temperature for crystallization is generally maintained at from about 212° F. to about 428° F., preferably from about 257° F. to about 392° F., and more preferably at around 329° F. for best results. The crystallizing material can be stirred or agitated as in a rocker bomb. Preferably, the crystallization temperature is maintained below the decomposition temperature of the organic template compound. Samples of material can be removed during crystallization to check the degree of crystallization and determine the optimum crystallization time.

The crystalline material formed can be separated and recovered by well-known means such as by filtration with washing. This material can be mildly dried for anywhere from a few hours to a few days at varying temperatures, typically ranging from about 77° F. to about 392° F., to form a dry cake. The dry cake can then be crushed to a powder or to small particles and extruded, pelletized, or made into forms suitable for its intended use. Typically, materials prepared after mild drying contain the organic template compound and water of hydration with the solid mass and a subsequent activation or calcination procedure is necessary, if it is desired to remove this material from the final product. Calcination is generally performed at temperatures ranging from about 500° F. to about 1562° F. and preferably from about 977° F. to about 1112° F. for best results. Extreme calcination temperatures or prolonged crystallization times may prove detrimental to the crystal structure or may destroy it. Generally there is minimal benefit in raising the calcination temperature beyond about 1112° F. in order to remove organic material from the originally formed crystalline material. The molecular sieve material can then be dried in a forced draft oven at about 329° F. for about 16 hours prior to calcination in air in a manner such that the temperature rise does not exceed 225° F. per hour. Once a temperature of about 1000° F. is reached, calcination temperature is maintained for about an additional 4 to 16 hours.

A catalytically active metal can also be placed onto the borosilicate structure through methods such as impregnation and ion-exchange. Suitable catalytically active metals can include metals of Groups IB, IIA, IIB, IIIA, IVB, VB, VIB, VIIB, and VIII, and rare earth elements.

Ion exchange and impregnation techniques for incorporation of such a catalytically active metal are well-known in the art. Typically, an aqueous solution of a cationic species is exchanged one or more times at about 25° C. to about 100° C. A hydrocarbon soluble metal compound such as a metal carbonyl also can be used to place a catalytically active material. Impregnation of a catalytically active material on the borosilicate or on a composition comprising the crystalline borosilicate suspended in and distributed throughout a matrix of a support material, such as a porous refractory inorganic oxide such as alumina and silica, often results in a suitable catalytic composition. A combination of ion exchange and impregnation can also be used.

The AMS-1B crystalline borosilicate molecular sieve in accordance with the present invention is generally admixed with or incorporated within various binders or matrix materials depending on the intended process use. The crystalline borosilicate molecular sieve can be combined with active or inactive materials, synthetic or naturally-occurring zeolites, as well as inorganic or organic materials which would be useful for binding the borosilicate. Well-known materials include silica, silica-alumina, alumina, alumina sols, hydrated aluminas, clays such as bentonite or kaolin, or other binders known in the art.

The preferred binder for use with the catalyst utilized in the present invention is silica. It has been found that use of a silica binder with the crystalline borosilicate molecular sieve provides improved n-Amylene conversion and i-Amylene selectivity resulting in improved i-Amylene yield compared to catalysts comprising an alumina binder. Under performance tests wherein the catalyst was exposed to steam at elevated temperatures, indicative of process conditions wherein the catalyst is undergoing periodic regeneration, the catalyst comprising a crystalline borosilicate molecular sieve with a silica binder provided substantially improved i-Amylene selectivity to catalyst comprising an alumina binder. Catalysts in accordance with the present invention and having silica binders are generally more hydrothermally stable than catalysts comprising other binders.

The catalyst in accordance with the process of the present invention generally comprises from about 20% by weight to about 99.99% by weight silica, preferably from about 50% by weight to about 99.99% by weight silica, and more preferably from about 70% by weight to about 95% by weight silica for best results. The term silica is defined in the generic sense and, for example, where the binder comprises an amorphous silicated alumina blend, the percentage of silica in the catalyst includes the weight present of silica present in the amorphous silicated alumina blend. The percentage of silica in the catalyst does not include silica present in the borosilicate molecular sieve component.

The borosilicate molecular sieve component is generally present in the catalyst in an amount ranging from about 0.01% by weight to about 50% by weight, preferably from about 0.01% by weight to about 30% by weight, and more preferably from about 1.0% by weight to about 15% by weight for best results. Crystalline borosilicate molecular sieve component concentrations as a percentage of the catalyst, in a range of from about 5% by weight to about 15% by weight, are particularly preferred because it has been found, that these particular sieve concentrations provide the best balance of n-Amylene conversion and i-Amylene selectivity, resulting in the highest yields of i-Amylene. Higher percentages of the molecular sieve component can result in high levels of n-Amylene conversion at the greater expense of excessively low i-Amylene selectivity. Lower percentages of the molecular sieve component can result in low n-Amylene conversion for which the higher i-Amylene selectivity cannot sufficiently compensate, resulting in lower i-Amylene yield.

Methods for dispersing molecular sieve materials within a matrix component are generally well-known to persons skilled in the art and applicable with respect to the borosilicate molecular sieve materials employed in accordance with the present invention. A preferred method is to blend the molecular sieve component, preferably in a finely divided form, into a sol, hydrosol, or hydrogel of an inorganic oxide, and then add a gelling medium such as ammonium hydroxide to the blend with stirring to produce a gel. The resulting gel can be dried, dimensionally formed if desired, and calcined. Drying is preferably conducted in air at a temperature of about 80° F. to about 350° F. (about 27° C. to about 177° C.) for a period of several seconds to several hours. Calcination is preferably conducted by heating in air at about 932° F. to about 1202° F. (about 500° C. to about 650° C.) for a period of time ranging from about 0.5 hours to about 16 hours.

Another suitable method for preparing a dispersion of molecular sieve component in a refractory inorganic oxide matrix component is to dry blend particles of each, preferably in finely divided form, and then to dimensionally form the dispersion if desired.

The isomerization process of the present invention can begin with an olefinic feedstock preheating step. The feedstock can be preheated in feed/reactor effluent heat exchangers prior to entering a furnace or contacting other high temperature waste heat means for final preheating to a targeted reaction zone inlet temperature. Suitable final preheating means, can include, but is not limited to waste heat from other refinery processes such as a fluid catalytic cracking unit, a fluidized or delayed coking unit, a catalytic hydrocracker, a crude distillation unit, a catalytic reforming unit, and hydrotreating units found in conventional petroleum refineries.

The feedstock can be contacted with a hydrogen stream prior to, during, and/or after preheating or may be operated in the substantial absence of hydrogen. The use of hydrogen in the process generally reduces the rate of catalyst deactivation, resulting in reduced catalyst regeneration requirements. Where the process utilizes hydrogen, the hydrogen-containing stream can be added before the isomerization reaction zone, in any one or more of the reactors in the reaction zone, or between reactors in a multiple reactor reaction zone.

The hydrogen stream can be pure hydrogen or can be in admixture with diluents such as low-boiling hydrocarbons, carbon monoxide, carbon dioxide, nitrogen, water, sulfur compounds, and the like. The hydrogen stream purity should be at least about 50% by volume hydrogen, preferably at least about 65% by volume hydrogen, and more preferably at least about 75% by volume hydrogen for best results. Hydrogen can be supplied from a hydrogen plant, a catalytic reforming facility, or other hydrogen-producing or hydrogen-recovery processes.

The reaction zone can include, but is not limited to, one or more fixed bed reactors containing the same or different catalysts, a moving column reactor and catalyst regeneration system, or a fluidized bed reactor and regenerator, with a fixed bed reactor process being preferred. The feedstock may be contacted with a catalyst or a catalyst bed in either upward, downward, or radial flow fashion with downflow being preferred. The reactants may be in the liquid phase, admixed liquid and vapor phase, or the vapor phase, with the best results obtained in the vapor phase.

Moving column reactors and regenerator systems such as that described in U.S. Pat. No. 3,647,680 to Greenwood et al. are known in the art and commonly used in processes such as catalytic reforming. The system generally comprises a vertical elongated reaction vessel comprising moving annular columns of catalyst wherein hydrocarbon is passed in out-to-in radial flow towards the center of the reaction vessel. Portions of the moving bed of catalyst are continuously directed to a regeneration system for regenerating the catalyst through combustion of coke components.

Fluidized bed reactors, which are commonly used in fluidized catalytic cracking and fluidized coking processes, fluidize the catalyst directly within the hydrocarbon feedstock, separate the catalyst from the reaction products, and direct the spent catalyst back to a regeneration zone for regeneration. The heat of reaction from the burning of coke from the catalyst generally supplies the heat requirements for sustaining the particular process reactions.

The preferred reaction zone facilities for use with the process of the present invention are fixed bed reactors. It is preferred that the isomerization reaction zone comprise at least two fixed bed reactors so as to facilitate on stream regeneration of the catalyst. The fixed bed reactors are generally equipped with proper manifolding to permit removal of each reactor from operation in a manner so as to provide for regeneration of the catalyst in that reactor while the other reactor or reactors sustain process operations. Fixed bed reactors in accordance with the present invention can also comprise a plurality of catalyst beds. The plurality of catalyst beds in a single fixed bed reactor can also comprise the same or different catalysts.

Since the isomerization reaction is generally mildly exothermic, interstage cooling, consisting of heat transfer devices between fixed bed reactors or between catalyst beds in the same reactor shell, can be employed. At least a portion of the heat generated from the isomerization process can often be profitably recovered for use in the isomerization process. A suitable heat sink for absorbing such heat provided by the isomerization reaction exotherm can and generally includes the feedstock preheat section of the isomerization process upstream of the isomerization reaction zone described hereabove. Where this heat recovery option is not available, cooling of the reaction zone effluent may be performed through cooling utilities such as cooling water or air, or through use of a hydrogen or hydrocarbon quench stream injected directly into the reactors. Multiple reactor processes can often provide reduced temperature exotherm per reactor shell and provide better isomerization reactor temperature control.

The isomerization reaction zone effluent is generally cooled and the effluent stream is directed to a separator device such as a stripper tower where light hydrocarbons formed during the reaction step can be removed and directed to more appropriate hydrocarbon pools. Where the process is performed in the presence of hydrogen, a separate hydrogen separation step can be performed upstream of and prior to light hydrocarbon separation. Some of the recovered hydrogen can be recycled back to the process while some of the hydrogen can be purged to external systems such as plant or refinery fuel. The hydrogen purge rate can be controlled to maintain minimum hydrogen purity. Recycled hydrogen is generally compressed, supplemented with "make-up" hydrogen, and reinjected into the process for further isomerization.

The stripper liquid effluent product is then generally conveyed to downstream processing facilities. The isomerized olefin product comprising a substantial portion of i-Amylene can be conveyed directly to a TAME production facility wherein i-Amylene can be converted, in the presence of methanol, to TAME. Prior to directing the isomerized olefin product to a TAME process, the stream can be purified by removal of non-i-Amylene components. For example, distillation steps can be used to remove hydrocarbons generally lighter than i-Amylene from the TAME feedstock. Similarly, heavier components can be removed through distillation steps by fractionating i-Amylene from the components heavier than i-Amylene. These non-i-amylene components can be directed to other, more economic refinery hydrocarbon pools.

Other separation steps in addition to, or instead of fractionation steps, can be utilized to further enhance the effectiveness of the process of the present invention. For example, the stripper liquid effluent product can be conveyed directly to (or after distillation concentration steps) a process facility for separating normal from isoamylenes. For example, the separation from normal hydrocarbons from branched chain and acyclic hydrocarbons can be effectively performed utilizing a solid sorbent. The preferred solid sorbents suitable for use in the process of the present invention are the molecular sieve type crystalline aluminosilicates having pore openings of a particular size so as to permit normal amylene components to enter the pores while excluding isoamylene and other non-linear components. Upon adsorption of the normal olefinic hydrocarbons on the molecular sieve, the branched hydrocarbons such as isoamylene, can be withdrawn from contact with the molecular sieve relatively free of normal olefinic hydrocarbons, and the normal olefinic hydrocarbons subsequently desorbed from the molecular sieve.

Wherein such a sorption step is performed, the stream comprising normal amylenes can be directed back to the process of the present invention to further increase isoamylene supply for the production of oxygenates such as TAME.

The catalyst utilized in the process of the present invention will generally require catalyst regeneration or replacement. It is anticipated that the catalyst utilized in the process of the present invention will generally require regeneration at least once every 800 hours, preferably at least once every 400 hours, and more preferably at least once every 200 hours for best results. The catalyst comprising borosilicate and a silica binder utilized in the process of the present invention is particularly suited for regeneration by the oxidation or burning of catalyst deactivating carbonaceous deposits with oxygen or an oxygen-containing gas. Moreover, catalyst performance is not generally diminished from periodic regeneration, in contradistinction to comparison catalysts tested. The term "regeneration," for purposes of the present invention, shall mean the recovery of at least a portion of the molecular sieve initial activity by combusting the coke deposits on the catalyst with oxygen or an oxygen-containing gas.

The prior art is replete with catalyst regeneration techniques that may be employed in the process of the present invention. Some of these regeneration techniques involve chemical methods of increasing the activity of deactivated molecular sieves. Others, including the preferred methods, relate to processes or methods for regenerating carbon (also known as coke) deactivated catalysts by the combustion of the coke with an oxygen-containing gas stream.

For example, U.S. Pat. No. 2,391,327 discloses the regeneration of catalysts contaminated with carbonaceous deposits with a cyclic flow of regeneration gases.

U.S. Pat. No. 3,755,961 relates to the regeneration of coke-containing crystalline zeolite molecular sieves which have been employed in an absorptive hydrocarbon separation process. The process involves the continuous circulation of an inert gas containing a quantity of oxygen in a closed loop arrangement through the bed of molecular sieve.

U.S. Pat. No. 4,480,144 relates to the use of a circulating gas to regenerate a coke deactivated zeolite-containing catalyst. The circulating gas is maintained at a low-moisture level by purging wet gases from the loop while simultaneously introducing dry gases into the loop. This method is particularly useful with zeolitic catalysts since zeolitic catalysts can be detrimentally effected by the presence of water. The catalyst of the present invention is particularly and substantially hydrothermally stable and resistant to the detrimental effects of water and steam.

The conditions and methods at which a catalyst may be regenerated by coke combustion can vary. It is typically desired to perform coke combustion at conditions of temperature, pressure, gas space velocity, etc. which are least damaging thermally to the catalyst being regenerated. It is also desired to perform the regeneration in a timely manner to reduce process down-time in the case of a fixed bed reactor system or equipment size in the case of a continuous regeneration process.

Optimum regeneration conditions and methods are generally disclosed in the prior art as mentioned hereabove. Catalyst regeneration is typically accomplished at conditions including a temperature range of from about 550° F. to about 1300° F., a pressure range of from about 0 psig to about 300 psig, and a regeneration gas oxygen content of from about 0.1 mole percent to about 23.0 mole percent. The catalyst in accordance with the process of the present invention maintained superior performance at conditions consistent with a regeneration temperature of as high as 1400° F. The oxygen content of the regeneration gas is typically increased during the course of a catalyst regeneration procedure based on catalyst bed outlet temperatures, in order to regenerate the catalyst as quickly as possible while avoiding catalyst-damaging process conditions.

The preferred catalyst regeneration conditions include a temperature ranging from about 600° F. to about 1150° F., a pressure ranging from about 0 psig to about 150 psig, and a regeneration gas oxygen content of about 0.1 mole percent to about 10 mole percent for best results.

Additionally, it is important that regeneration be accomplished in the presence of an oxygen-containing gas. The oxygen-containing regeneration gas typically comprises nitrogen and carbon combustion products such as carbon monoxide and carbon dioxide, to which oxygen in the form of air has been added. However, it is possible that the oxygen can be introduced into the regeneration gas as pure oxygen, or as a mixture of oxygen diluted with another gaseous component. Air is the preferred oxygen-containing gas.

Operating conditions to be used in the isomerization process of the present invention include an average reaction zone temperature of from about 500° F. to about 1200° F., preferably from about 500° F. to about 1000° F., and more preferably from about 600° F. to about 1000° F. for best results. Reaction temperatures below these ranges can result in reduced n-Amylene conversion and lower i-Amylene yield. Reaction temperatures above these ranges can result in reduced i-Amylene selectivity and lower i-Amylene yields.

The process of the present invention generally operates at reaction zone pressures ranging from as low as substantially vacuum pressure (about 0 to about 27.6 inches of water vacuum) to about 1200 psig, preferably from about 0 psig to about 200 psig, and more preferably from about 0 psig to about 100 psig for best results. Where the process operates in the presence of hydrogen, hydrogen circulation rates generally range from about 200 SCF/Bbl to about 20,000 SCF/Bbl, preferably from about 200 SCF/Bbl to about 10,000 SCF/Bbl, and most preferably from about 200 to about 2000 SCF/Bbl for best results. Reaction pressures and hydrogen circulation rates below these ranges can result in higher catalyst deactivation rates resulting in increased energy intensive regeneration cycles. Excessively high reaction pressures increase energy and equipment costs and provide diminishing marginal benefits.

The process of the present invention generally operates at a weight hourly space velocity (WHSV) of from about 4 $hr^{-1}$ to about 32 $hr^{-1}$, preferably from about 10 $hr^{-1}$ to about 32 $hr^{-1}$, and most preferably from about 10 $hr^{-1}$ to about 26 $hr^{-1}$ for best results. Feed space velocities exceeding the levels described herein generally result in a decline in n-Amylene conversion which outpaces the gain i-Amylene selectivity, resulting in substantially lower i-Amylene yield. Feed space velocities short of the levels described herein generally result in an increase in n-Amylene conversion but a larger reduction in i-Amylene selectivity, resulting in reduced i-Amylene yields.

The olefin isomerization process of the present invention provides several benefits over the prior art processes.

The process of the present invention cost-effectively increases oxygenate production capability by increasing i-Amylene feedstock availability. The present invention increases the volume of i-Amylenes by increasing the proportion of i-Amylenes to total Amylenes derived from facilities such as fluid cracking units, fluidized or delayed cokers, and dehydrogenation facilities. For example, the process of the present invention can convert in excess of 40 percent of the normal amylene fraction of an olefinic hydrocarbon feedstream comprising about 50 weight percent normal amylene to isoamylene. Typically, the process of the present invention can convert in excess of 50 percent of the normal amylene fraction of an olefinic hydrocarbon feedstream comprising about 50 weight percent normal amylene to isoamylene. Under many scenarios, conversion of the normal amylene fraction of an olefinic hydrocarbon feedstream comprising about 50 weight percent normal amylene to isoamylene, can exceed 62 percent. The i-Amylenes can be subsequently converted to TAME.

The process of the present invention can be operated reliably and effectively under conditions wherein the catalyst undergoes periodic regeneration. The catalyst utilized in the present invention is particularly hydrothermally stable and maintains superior i-Amylene yield performance under scenarios wherein the catalyst is exposed to conditions encountered in conventional regeneration systems. Under conditions wherein the catalyst in accordance with the present invention is undergoing periodic regeneration, conversion of the normal amylene fraction of an olefinic hydrocarbon feedstream 1B-3 borosilicate sieve, the CAB-O-SIL EH-5 silica, and Catalyst 1 are provided in Table 1.

TABLE 1

|  | HAMS-1B-3/CAB-O-SIL Silica | HAMS-1B-3 | CAB-O-SIL Silica |
| --- | --- | --- | --- |
| HAMS-1B-3, wt % | 10 | 100 | — |
| Silica, wt % | 90 | — | 100 |
| Alumina, wt % | — | — | — |
| Na, ppm | 25 | 80 | — |
| Al, ppm | 40 | 270 | — |
| Fe, ppm | 32 | 240 | — |
| Boron, wt % | 0.11 | 1.45 | — |
| Crystallinity HAMS-1B-3, wt % (XRD) | 9 | 95 | — |
| Pore Volume, cc/gram | 1.24 | 0.07 | 1.23 |
| BET Area, m2/gram | 312 | 317 | 339 | comprising about 50 weight percent normal amylene to isoamylene, generally exceeds 45 percent, typically exceeds 53 percent, and can exceed 58 percent. As can be seen from the above, the process of the present invention provides superior performance under both regenerative and non-regenerative conditions.

The process of the present invention can operate effectively in the presence of or without hydrogen. Although operation of the present process in the presence of hydrogen reduces catalyst deactivation rates and the magnitude of regeneration required, the process can be effectively operated without hydrogen. Hydrogen supply facilities which generally require compression equipment, hydrogen separation systems, and sophisticated metallurgy can substantially reduce the cost effectiveness of the process.

The process of the present invention can accommodate a stand alone operating facility or incorporation with existing process units. The present invention generally requires a feedstock preheat system, a reaction system, and regeneration facilities. Such facilities can be added to the tail end of a fluid catalytic cracking unit, the feed or product recovery sections of a TAME facility, the feed or product recovery sections of a dehydrogenation unit, or to any one or more of several refinery facilities wherein advantages, such as access to waste heat, hydrogen, feed or product systems, or operating personnel can be obtained.

The present invention is described in further detail in connection with the following examples, it being understood that the same are for purposes of illustration and not limitation.

EXAMPLE 1

An olefin isomerization catalyst in accordance with the present invention and comprising about 10 percent by weight of a borosilicate molecular sieve and about 90 percent by weight of a silica binder was prepared by mixing 45.1 grams of CAB-O-SIL EH-5 silica and 250 grams of distilled water in a small waring blender for a period of about 5 minutes. The above mixture was supplemented with 5.0 grams of calcined and ammonium exchanged HAMS-1B-3 borosilicate molecular sieve and mixed for an additional 5 minutes. The HAMS-1B-3 borosilicate sieve material was prepared in a manner similar to that described in European Patent No. 0184461 to Haddad et al. and U.S. Pat. No. 4,725,570 to Haddad et al., the disclosures of which are hereby incorporated by reference. The mixture was dried at 250° F. for 16 hours in a forced air oven. The dried mixture was crushed, sized to 12 to 20 mesh (U.S. Sieve Series), and calcined at 1000° F. for 3 hours. The catalyst was designated as Catalyst 1. The properties of the HAMS-1B-3 borosilicate sieve, the CAB-O-SIL EH-5 silica, and Catalyst 1 are provided in Table 1.

EXAMPLE 2

A comparison olefin isomerization catalyst comprising about 10 percent by weight of a borosilicate molecular sieve and about 90 percent by weight of an alumina binder was prepared with a HAMS-1B-3 borosilicate molecular sieve material. The HAMS-1B-3 borosilicate sieve material was also prepared in a manner similar to that described in European Patent No. 0 184 461 to Haddad et al. and U.S. Pat. No. 4,725,570 to Haddad et al. The catalyst was prepared by mixing 10.4 grams of calcined and ammonium exchanged HAMS-1B-3 borosilicate molecular sieve powder with 124.4 grams of Catapal SB alumina (alpha-alumina monohydrate manufactured by Vista). An extrusion aid was added to the mixed solids consisting of 15.0 grams of ammonium acetate, 10.1 grams of hydroxyethylcellulose, and 10.3 grams of glycerin dissolved in 30.0 grams of distilled water. The solids mixture was further moistened with distilled water and extruded into 1/16 inch extrudates. The extrudate was dried at 250° F. for 16 hours in a forced air oven and calcined at 1000° F. for 3 hours. The extrudates were crushed and sized to 12 to 20 mesh (U.S. Sieve Series). The catalyst was designated as Catalyst 2.

EXAMPLE 3

A comparison olefin isomerization catalyst comprising about 5 percent by weight of a borosilicate molecular sieve and about 95 percent by weight of an alumina binder was prepared with a HAMS-1B-3 borosilicate molecular sieve material. The HAMS-1B-3 borosilicate sieve material was also prepared in a manner similar to that described in European Patent No. 0 184 461 to Haddad et al. and U.S. Pat. No. 4,725,570 to Haddad et al. The catalyst was prepared by mixing 5.0 grams of calcined and ammonium exchanged HAMS-1B-3 borosilicate molecular sieve powder with 131.8 grams of Catapal SB alumina (alpha-alumina monohydrate manufactured by Vista). The solids mixture was added to 68.5 grams of distilled water and extruded into 1/16 inch extrudates. The extrudate was dried at 250° F. for 16 hours in a forced air oven and calcined at 1000° F. for 3 hours. The extrudates were crushed and sized to 12 to 20 mesh (U.S. Sieve Series). The catalyst was designated as Catalyst 3.

EXAMPLE 4

A comparison olefin isomerization catalyst comprising about 5.3 percent by weight of silica and about 94.7 percent by weight of an alumina binder was prepared by extruding Calcined Versal 450 Alumina (manufactured by LaRoche Chemicals) into 1/16 inch extrudates. The alumina extrudates were dried at 250° F. for 16 hours in a forced air oven and calcined at 930° F. for 3 hours. The extrudates were crushed and sized to 12 to 20 mesh (U.S. Sieve Series).

A mixture of 28.2 grams of tetraethyl orthosilicate and 150 grams of normal hexane was prepared and added to 142.2 grams of the alumina extrudates and mixed well. The normal hexane was allowed to evaporate over a period of 5 hours. The extrudate particles were dried in a forced air oven at 212° F. for 16 hours and calcined at 1000° F. for 8 hours. The catalyst was designated as Catalyst 4.

EXAMPLE 5

A comparison olefin isomerization catalyst comprising about 0.8 percent by weight of fluoride and about 99.2 percent by weight of an alumina binder was prepared using incipient wetness impregnation techniques. A solution of 500 grams of Catapal SB alumina (alpha-alumina monohydrate manufactured by Vista) was combined with 7 grams of ammonium fluoride and 350 grams of distilled water and mixed well. The mixture was dried at 250° F. for 16 hours in a forced air oven.

The dried catalyst was added to 322 grams of distilled water and the resulting mixture was extruded into 1/16 inch extrudates. The extrudate was dried at 250° F. for 16 hours in a forced air oven and calcined at 950° F. for 5 hours. The extrudates were crushed and sized to 12 to 20 mesh (U.S. Sieve Series). The catalyst was designated as Catalyst 5.

EXAMPLE 6

A comparison olefin isomerization catalyst comprising about 60 percent by weight of a borosilicate molecular sieve and about 40 percent by weight of a silica binder was prepared by intimately mixing 168 grams of HAMS-1B-3 borosilicate molecular sieve powder with 112 grams of CAB-O-SIL EH-5 silica. The mixed solids were added to 250 grams of distilled water and blended in a small waring blender for a period of about 5 minutes. The mixture was dried at 250° F. for 16 hours in a forced air oven. The dried solid was ground to less than 20 mesh size (U.S. Sieve Series).

A solution of 37 grams of ammonium acetate, 16 grams of glycerine, and 189 grams of distilled water was added to the dried catalyst. The resulting mixture was extruded into 1/16 inch extrudates. The extrudate was dried at 250° F. for 16 hours in a forced air oven and calcined at 1000° F. for 3 hours. The extrudates were crushed and sized to 12 to 20 mesh (U.S. Sieve Series). The catalyst was designated as Catalyst 6.

EXAMPLE 7

A comparison olefin isomerization catalyst comprising about 78 percent by weight of a borosilicate molecular sieve and about 22 percent by weight of an alumina binder was prepared by mixing 200.0 grams of calcined and ammonium exchanged HAMS-1B-3 borosilicate molecular sieve powder with 80.0 grams of Catapal SB alumina (alpha-alumina monohydrate manufactured by Vista). The solids mixture was added to 146.0 grams of distilled water and extruded into 1/16 inch extrudates. The extrudate was dried at 250° F. for 16 hours in a forced air oven and calcined at 1000° F. for 3 hours. The extrudates were crushed and sized to 12 to 20 mesh (U.S. Sieve Series). The catalyst was designated as Catalyst 7.

EXAMPLE 8

A comparison olefin isomerization catalyst comprising about 5 percent by weight of a gallosilicate molecular sieve and about 95 percent by weight of an alumina binder was prepared by dissolving 223 grams of sodium hydroxide, 78 grams of gallium oxide, 1465 grams of tetrapropyl ammonium bromide, 548 grams of 2,4 pentanedione, and 3568 grams of a silica sol (Ludox HS-40 manufactured by Ludox Corporation) in 10,300 grams of distilled water in an autoclave. The autoclave was sealed and maintained at a temperature of between about 215° F. (102° C.) and about 285° F. (140° C.), autogenous pressure, and at a mixer speed ranging from about 200 rpm to about 333 rpm for a period of about 120 hours. The slurry was filtered and washed and the cake dried in an oven at 250° F. (121° C.) for a period of 12 hours. The dried filter cake was then calcined at 1000° F. (538° C.) for a period of 4 hours.

The filter cake was ion exchanged with ammonium nitrate in water and heated, under reflux, at a temperature of about 160° F. (71° C.) for a period of 4 hours. The slurry was allowed to cool while stirring for 2 hours and allowed to settle for a period of 12 hours. The slurry was decanted and filtered leaving a filter cake. The filter cake was calcined at 1000° F. (538° C.) for a period of 4 hours, ion exchanged two more times in accordance with the above procedure, and washed with water.

The gallosilicate was dispersed in the alumina by mixing 5.0 grams of the gallosilicate molecular sieve powder with 131.8 grams of Catapal SB alumina (alpha-alumina monohydrate manufactured by Vista). The solids mixture was added to 68.8 grams of distilled water and extruded into 1/16 inch extrudates. The extrudate was dried at 250° F. for 16 hours in a forced air oven and calcined at 1000° F. for 3 hours. The extrudates were crushed and sized to 12 to 20 mesh (U.S. Sieve Series). The catalyst was designated as Catalyst 8.

EXAMPLE 9

A comparison olefin isomerization catalyst comprising about 5 percent by weight of beta zeolite and about 95 percent by weight of an alumina binder was prepared from a mixture containing tetraethylammonium hydroxide, distilled water, sodium aluminate (Nalco 680), and colloidal silica (Ludox HS-40). The solution was crystallized at 302° F. for 136 hours and the crystallized beta zeolite was washed with water and filtered. The filtered crystallized beta zeolite was dried at 221° F. and calcined at 1022° F. for 6 hours. The beta zeolite was ion-exchanged by mixing with ammonium nitrate and water, stirring, and filtering. The filtered beta zeolite particulate was dried for 12 hours at 482° F.

The beta zeolite particulate was dispersed in the alumina by mixing 5.0 grams of the beta zeolite powder with 131.8 grams of Catapal SB alumina (alpha-alumina monohydrate manufactured by Vista). The solids mixture was added to 74.7 grams of distilled water and extruded into 1/16 inch extrudates. The extrudate was dried at 250° F. for 16 hours in a forced air oven and calcined at 1000° F. for 3 hours. The extrudates were crushed and sized to 12 to 20 mesh (U.S. Sieve Series). The catalyst was designated as Catalyst 9.

EXAMPLE 10

A comparison olefin isomerization catalyst comprising about 5 percent by weight of ZSM-5 and about 95 percent by weight of an alumina binder was prepared by mixing 5.0 grams of ZSM-5 (silicalite powder S-115 manufactured by Union Carbide having a silicon to aluminum molar ratio of 180) with 131.8 grams of Catapal SB alumina (alpha-alumina monohydrate manufactured by Vista. The solids mixture was added to 74.7 grams of distilled water and extruded into 1/16 inch extrudates. The extrudate was dried at 250° F. for 16 hours in a forced air oven and calcined at 1000° F. for 3 hours. The extrudates were crushed and sized to 12 to 20 mesh (U.S. Sieve Series). The catalyst was designated as Catalyst 10.

EXAMPLE 11

A feedstock consisting of normal pentane, isopentane, and 1-penetene was prepared for processing with catalysts in accordance with the present invention and with comparison catalysts. Details of the feedstock composition are provide in Table 2.

TABLE 2

| FEEDSTOCK COMPOSITION | WT % |
|---|---|
| METHANE | 0.00 |
| ETHANE | 0.00 |
| ETHYLENE | 0.00 |
| PROPYLENE | 0.00 |
| PROPANE | 0.00 |
| ISOBUTANE | 0.00 |
| N-BUTANE | 0.00 |
| N-BUTYLENES | 0.00 |
| ISOBUTYLENE | 0.00 |
| N-PENTANE | 0.38 |
| ISOPENTANE | 49.52 |
| 1-PENTENE | 49.22 |
| TRANS-2-PENTENE | 0.15 |
| CIS-2-PENTENE | 0.04 |
| 3-M-1-BUTENE | 0.00 |
| 2-M-1-BUTENE | 0.40 |
| 2-M-2-BUTENE | 0.20 |
| C6+ | 0.09 |
| | 100.00 |

EXAMPLE 12

The feedstock of Example 11 was isomerized over Catalysts 1 through 10 described in Examples 1 through 10. All catalysts were tested using a quartz bench-top reactor unit featuring a quartz tube reactor containing a packed bed. Operation was downflow with once-through hydrocarbon flow. Catalyst of 12 to 20 mesh size (U.S. Sieve Series) was used for testing and the catalyst was positioned between a top and bottom bed of 30 to 50 mesh size (U.S. Sieve Series) alpha alumina. The feedstock of Example 11 was processed through the quartz bench-top unit at varied experimental run lengths. The products were condensed into liquid fractions for all experiments and analyzed on a Hewlett-Packard Model 5890 gas chromatograph equipped with a 100 meter Quadrex Corporation OV-101 methyl silicone capillary column. The data was analyzed using an IBM mainframe computer program.

The catalysts were evaluated with respect to normal amylene conversion (n-Amylene Conv.), isoamylene selectivity (i-Amylene Sel.), and isoamylene yield (i-Amylene Yield). These parameters were calculated by weight and in accordance with the following models:

$$\text{n-Amylene Conv.} = \frac{\Sigma\text{n-Amylene(feed)} - \Sigma\text{n-Amylene(product)}}{\Sigma\text{n-Amylene(feed)}}$$

$$\text{i-Amylene Sel.} = \frac{\Sigma\text{i-Amylene(product)} - \Sigma\text{i-Amylene(feed)}}{\Sigma\text{n-Amylene(feed)} - \Sigma\text{n-Amylene(product)}}$$

$$\text{i-Amylene Yield} = \frac{(\text{i-Amylene Sel.}) \times (\text{n-Amylene Conv.})}{100}$$

There was no attempt to simulate the effect of catalyst regeneration inhetent to many processes in accordance with the present invention or the effects of such regeneration on catalyst performance. The catalyst composition, process conditions, and product yields, conversions, and selectivities of Catalysts 1 through 10 described in Examples 1 through 10, are specified in Table 3.

TABLE 3

| | CATALYST | | | | |
|---|---|---|---|---|---|
| | 1<br>10% HAMS-1B-3/<br>90% Silica | 2<br>10% HAMS-1B-3/<br>90% Alumina | 3<br>5% HAMS-1B-3/<br>95% Alumina | 4<br>SILICATED/<br>ALUMINA | 5<br>FLUORIDED/<br>ALUMINA |
| Process Conditions | | | | | |
| Reaction Temp., F. | 700.00 | 700.00 | 700.00 | 700.00 | 700.00 |
| Pressure, atm | 1.00 | 1.00 | 1.00 | 1.00 | 1.00 |
| Feed WHSV, hr-1 | 16.00 | 16.00 | 16.00 | 4.00 | 4.00 |
| 1-Pentene WHSV, HR-1 | 8.00 | 8.00 | 8.00 | 2.00 | 2.00 |
| Product Compositions (wt. %) | | | | | |
| METHANE | 0.00 | 0.00 | 0.00 | 0.00 | 0.00 |
| ETHANE | 0.00 | 0.00 | 0.00 | 0.00 | 0.00 |
| ETHYLENE | 0.00 | 0.00 | 0.00 | 0.00 | 0.00 |
| PROPYLENE | 0.18 | 0.45 | 0.37 | 0.10 | 0.14 |
| PROPANE | 0.00 | 0.00 | 0.00 | 0.00 | 0.00 |
| ISOBUTANE | 0.00 | 0.04 | 0.02 | 0.03 | 0.01 |
| N-BUTANE | 0.00 | 0.00 | 0.00 | 0.00 | 0.00 |
| N-BUTYLENES | 0.69 | 1.11 | 0.98 | 0.30 | 0.46 |
| ISOBUTYLENE | 0.46 | 0.99 | 0.81 | 0.62 | 0.68 |
| N-PENTANE | 0.44 | 0.45 | 0.45 | 0.61 | 0.45 |
| ISOPENTANE | 50.06 | 51.43 | 50.18 | 50.51 | 50.38 |
| 1-PENTENE | 1.59 | 2.30 | 1.83 | 1.81 | 1.65 |
| TRANS-2-PENTENE | 6.61 | 8.94 | 7.15 | 8.46 | 7.08 |
| CIS-2-PENTENE | 3.26 | 4.48 | 3.56 | 4.00 | 3.48 |
| 3-M-1-BUTENE | 1.08 | 0.96 | 1.06 | 0.87 | 1.06 |
| 2-M-1-BUTENE | 8.60 | 7.21 | 7.94 | 7.40 | 8.49 |
| 2-M-2-BUTENE | 23.34 | 18.58 | 20.73 | 22.00 | 23.95 |

TABLE 3-continued

| CATALYST | | | | | |
|---|---|---|---|---|---|
| C6+ | 3.69 | 3.06 | 4.92 | 3.29 | 2.17 |
| Results | 100.00 | 100.00 | 100.00 | 100.00 | 100.00 |
| n-Amylene Conv. (%) | 76.81 | 68.18 | 74.62 | 71.12 | 75.29 |
| Isoamylene Sel. (%) | 85.43 | 77.62 | 79.01 | 84.43 | 88.44 |
| Isoamylene Yld. (%) | 65.62 | 52.92 | 58.96 | 60.05 | 66.59 |

| | 6<br>60% HAMS/<br>40% Silica | 7<br>78% HAMS-1B-3/<br>22% Alumina | 8<br>5% GaMS/<br>95% ALUMINA | 9<br>5% BETA/<br>95% ALUMINA | 10<br>5% SILICALITE/<br>95% ALUMINA |
|---|---|---|---|---|---|
| Process Conditions | | | | | |
| Reaction Temp., F. | 700.00 | 700.00 | 700.00 | 700.00 | 700.00 |
| Pressure, atm | 1.00 | 1.00 | 1.00 | 1.00 | 1.00 |
| Feed WHSV, hr-1 | 16.00 | 16.00 | 16.00 | 16.00 | 16.00 |
| 1-Pentene WHSV, HR-1 | 8.00 | 8.00 | 8.00 | 8.00 | 8.00 |
| Product Compositions (wt. %) | | | | | |
| METHANE | 0.00 | 0.00 | 0.00 | 0.00 | 0.00 |
| ETHANE | 0.00 | 0.00 | 0.00 | 0.00 | 0.00 |
| ETHYLENE | 0.01 | 0.00 | 0.00 | 0.00 | 0.00 |
| PROPYLENE | 0.92 | 0.89 | 0.10 | 0.09 | 1.56 |
| PROPANE | 0.01 | 0.06 | 0.01 | 0.00 | 0.02 |
| ISOBUTANE | 0.09 | 0.73 | 0.21 | 0.07 | 0.17 |
| N-BUTANE | 0.00 | 0.17 | 0.08 | 0.01 | 0.07 |
| N-BUTYLENES | 2.77 | 4.47 | 3.03 | 0.32 | 4.55 |
| ISOBUTYLENE | 2.19 | 3.43 | 2.11 | 0.46 | 3.56 |
| N-PENTANE | 0.50 | 0.76 | 0.75 | 0.51 | 0.65 |
| ISOPENTANE | 53.08 | 59.42 | 56.84 | 50.77 | 53.04 |
| 1-PENTENE | 1.24 | 0.65 | 0.66 | 4.13 | 1.04 |
| TRANS-2-PENTENE | 5.01 | 2.60 | 2.70 | 15.53 | 3.94 |
| CIS-2-PENTENE | 2.49 | 1.29 | 1.41 | 7.79 | 2.02 |
| 3-M-1-BUTENE | 0.96 | 0.45 | 0.42 | 0.71 | 0.69 |
| 2-M-1-BUTENE | 6.91 | 3.55 | 3.39 | 4.92 | 5.32 |
| 2-M-2-BUTENE | 17.80 | 9.46 | 9.78 | 12.97 | 14.02 |
| C6+ | 6.02 | 12.07 | 18.51 | 1.72 | 9.35 |
| Results | 100.00 | 100.00 | 100.00 | 100.00 | 100.00 |
| n-Amylene Conv. (%) | 82.31 | 90.81 | 90.35 | 44.44 | 85.83 |
| Isoamylene Sel. (%) | 61.64 | 28.66 | 30.33 | 81.97 | 45.81 |
| Isoamylene Yld. (%) | 50.74 | 26.03 | 27.40 | 36.43 | 39.32 |

Catalyst 1, consisting of about 10 percent by weight of a borosilicate molecular sieve and about 90 percent by weight silica provided outstanding n-Amylene conversion, i-Amylene selectivity, and resultant i-Amylene yield.

Catalyst 2, consisting of about 10 percent by weight borosilicate molecular sieve and about 90 percent by weight alumina provided average n-Amylene conversion, average i-Amylene selectivity, resulting in average i-Amylene yield. Catalyst 2, containing 90 weight percent of an alumina binder instead of 90 weight percent of a silica binder as provided in Catalyst 1, provided inferior performance to that of Catalyst 1.

Catalyst 3, consisting of about 5 percent by weight of a borosilicate molecular sieve and about 95 percent by weight of alumina provided outstanding n-Amylene conversion, i-Amylene selectivity, and resultant i-Amylene yield. Catalyst 3 containing 95 weight percent of an alumina binder compared to 90 weight percent of an alumina binder for Catalyst 2 provided improved n-Amylene conversion, i-Amylene selectivity, and resultant i-Amylene yield to that of Catalyst 2. Catalyst 3 performance was clearly inferior to the performance of Catalyst 1, the catalyst used in the process of the present invention, for all parameters measured.

Catalyst 4, consisting of about 5.3 percent by weight silica and about 94.7 percent by weight alumina also provided outstanding n-Amylene conversion, i-Amylene selectivity, and resultant i-Amylene yield. Catalyst 4 containing silica and alumina components without a borosilicate component provided improved performance levels to that of Catalyst 2 and inferior performance levels to that of Catalyst 3 containing borosilicate and alumina, and inferior performance to that of Catalyst 1 containing borosilicate and silica.

Catalyst 5, consisting of about 0.8 percent by weight fluoride and about 99.2 percent by weight alumina provided outstanding n-Amylene conversion, i-Amylene selectivity, and resultant i-Amylene yield. Catalyst 5 containing minor amounts of fluoride and alumina without a borosilicate component provided superior performance to that of Catalyst 2 and 3 containing borosilicate and alumina and was similar in level of performance to Catalyst 1 containing borosilicate and silica.

Catalyst 6, consisting of about 60 percent by weight of a borosilicate molecular sieve and about 40 percent by weight silica provided outstanding n-Amylene conversion, but only average i-Amylene selectivity, resulting in average i-Amylene yield. Catalyst 6 containing large amounts of borosilicate with a silica binder was inferior to Catalysts 1, 2, and 3 containing substantially lower amounts of borosilicate.

Catalyst 7, consisting of about 78 percent by weight of a borosilicate molecular sieve and about 22 percent by weight alumina provided n-Amylene conversion superior to that of all catalysts tested but poor i-Amylene selectivity, resulting in poor overall i-Amylene yield. Catalyst 7 containing large amounts of borosilicate with an alumina binder was inferior to Catalysts 1, 2, and 3 having substantially lower amounts of borosilicate and was inferior to Catalyst 6 having a lower amount of borosilicate with silica substituted for the alumina.

Catalyst 8, consisting of about 5 percent by weight of a gallosilicate molecular sieve and about 95 percent by weight of alumina provided outstanding n-Amylene conversion but poor i-Amylene selectivity, resulting in poor i-Amylene yield. Catalyst 8 containing a gallosilicate component was clearly inferior to Catalyst 3 containing an identical amount of a borosilicate component.

Catalyst 9, consisting of about 5 percent by weight of beta zeolite and about 95 percent by weight of alumina provided poor n-Amylene conversion but outstanding i-Amylene selectivity, still resulting, however, in poor i-Amylene yield. Catalyst 9 containing a beta zeolite component was clearly inferior to catalyst 3 containing an identical amount of a borosilicate component.

Catalyst 10, consisting of about 5 percent by weight of ZSM-5 silicalite and about 95 percent by weight of alumina provided outstanding n-Amylene conversion but poor i-Amylene selectivity, resulting in poor i-Amylene yield. Catalyst 10 containing a silicalite ZSM-5 component was clearly inferior to Catalyst 3 containing an identical amount of a borosilicate component.

EXAMPLE 13

The catalyst in accordance with the present invention, Catalyst 1, and comparison Catalysts 2-5, and 8-10, were steamed in a manner so as to simulate catalyst performance in a commerical environment where each catalyst can undergo periodic and routine catalyst regeneration cycles. Steamings of the above catalysts were performed in a fixed-bed, up-flow quartz reactor by loading 10-15 grams of the catalyst into the reactor. The reactor was maintained under a nitrogen purge and heated to about 1000° F. Once the reactor reached 1000° F., the nitrogen flow was terminated and a flow of water initiated. Time of steaming commenced upon first detection of steam exiting the quartz reactor. Steaming continued for a period of about 5 hours, after which the stream of water was stopped and the reactor and catalyst cooled to about 70° F.

The steamed catalysts were tested in a manner similar to that described in Example 12. The catalyst composition, process conditions, and product yields, conversions, and selectivities of Catalysts 1 through 5, and 8 through 10 described in Examples 1 through 5 and Examples 8 through 10, are specified in Table 4.

TABLE 4

| | CATALYST | | | | |
|---|---|---|---|---|---|
| | 1 STEAMED 10% HAMS/90% SILICA | 2 STEAMED 10% HAMS-1B-3/90% ALUMINA | 3 STEAMED 5% HAMS/95% ALUMINA | 4 STEAMED SiO2/ ALUMINA | 5 STEAMED F/ALUMINA |
| Process Conditions | | | | | |
| Reaction Temp., F. | 700.00 | 700.00 | 700.00 | 700.00 | 700.00 |
| Pressure, atm | 1.00 | 1.00 | 1.00 | 1.00 | 1.00 |
| Feed WHSV, hr-1 | 16.00 | 16.00 | 16.00 | 4.00 | 4.00 |
| 1-Pentene WHSV, HR-1 | 8.00 | 8.00 | 8.00 | 2.00 | 2.00 |
| Product Compositions (wt. %) | | | | | |
| METHANE | 0.00 | 0.00 | 0.00 | 0.00 | 0.00 |
| ETHANE | 0.00 | 0.00 | 0.00 | 0.00 | 0.00 |
| ETHYLENE | 0.00 | 0.00 | 0.00 | 0.00 | 0.00 |
| PROPYLENE | 0.22 | 1.52 | 1.14 | 0.04 | 0.03 |
| PROPANE | 0.00 | 0.01 | 0.00 | 0.00 | 0.00 |
| ISOBUTANE | 0.00 | 0.15 | 0.10 | 0.00 | 0.00 |
| N-BUTANE | 0.00 | 0.00 | 0.00 | 0.00 | 0.00 |
| N-BUTYLENES | 1.15 | 3.04 | 3.78 | 0.08 | 0.15 |
| ISOBUTYLENE | 0.52 | 2.62 | 2.71 | 0.22 | 0.23 |
| N-PENTANE | 0.45 | 0.49 | 0.56 | 0.42 | 0.40 |
| ISOPENTANE | 50.04 | 55.74 | 53.99 | 49.98 | 50.02 |
| 1-PENTENE | 1.61 | 1.38 | 1.01 | 2.82 | 2.69 |
| TRANS-2-PENTENE | 6.50 | 5.58 | 3.88 | 15.44 | 11.85 |
| CIS-2-PENTENE | 3.24 | 2.77 | 1.95 | 6.97 | 5.78 |
| 3-M-1-BUTENE | 0.95 | 0.72 | 0.76 | 0.55 | 0.87 |
| 2-M-1-BUTENE | 8.66 | 5.68 | 5.76 | 4.91 | 7.22 |
| 2-M-2-BUTENE | 22.85 | 14.71 | 14.54 | 17.05 | 20.21 |
| C6+ | 3.81 | 5.59 | 9.82 | 1.52 | 0.55 |
| Results | 100.00 | 100.00 | 100.00 | 100.00 | 100.00 |
| n-Amylene Conv. (%) | 77.03 | 80.31 | 86.16 | 48.94 | 58.87 |
| Isoamylene Sel. (%) | 83.71 | 51.69 | 48.06 | 90.61 | 95.22 |
| Isoamylene Yld. (%) | 64.48 | 41.51 | 41.41 | 44.34 | 56.06 |

| | 8 STEAMED 5% GaMS/ 95% ALUMINA | 9 STEAMED 5% BETA/ 95% ALUMINA | 10 STEAMED 5% SILICALITE/ 95% ALUMINA |
|---|---|---|---|
| Process Conditions | | | |
| Reaction Temp., F. | 700.00 | 700.00 | 700.00 |
| Pressure, atm | 1.00 | 1.00 | 1.00 |
| Feed WHSV, hr-1 | 16.00 | 16.00 | 16.00 |
| 1-Pentene WHSV, HR-1 | 8.00 | 8.00 | 8.00 |
| Product Compositions (wt. %) | | | |
| METHANE | 0.00 | 0.00 | 0.00 |
| ETHANE | 0.00 | 0.00 | 0.00 |
| ETHYLENE | 0.01 | 0.00 | 0.00 |
| PROPYLENE | 1.47 | 0.11 | 1.68 |

TABLE 4-continued

| CATALYST | | | |
|---|---|---|---|
| PROPANE | 0.01 | 0.00 | 0.03 |
| ISOBUTANE | 0.12 | 0.04 | 0.20 |
| N-BUTANE | 0.04 | 0.00 | 0.00 |
| N-BUTYLENES | 3.40 | 0.28 | 4.96 |
| ISOBUTYLENE | 2.74 | 0.46 | 3.82 |
| N-PENTANE | 0.58 | 0.50 | 0.69 |
| ISOPENTANE | 52.12 | 50.93 | 53.18 |
| 1-PENTENE | 1.14 | 4.20 | 0.90 |
| TRANS-2-PENTENE | 4.46 | 16.21 | 3.53 |
| CIS-2-PENTENE | 2.31 | 8.06 | 1.84 |
| 3-M-1-BUTENE | 0.81 | 0.67 | 0.62 |
| 2-M-1-BUTENE | 5.98 | 4.72 | 4.80 |
| 2-M-2-BUTENE | 15.51 | 12.29 | 13.00 |
| C6+ | 9.30 | 1.53 | 10.75 |
| Results | 100.00 | 100.00 | 100.00 |
| n-Amylene Conv. (%) | 83.99 | 42.38 | 87.31 |
| Isoamylene Sel. (%) | 52.29 | 81.57 | 41.31 |
| Isoamylene Yld. (%) | 43.92 | 34.57 | 36.07 |

Steamed Catalyst 1, consisting of about 10 percent by weight of a borosilicate molecular sieve and about 90 percent by weight silica provided surprisingly similar n-Amylene conversion, i-Amylene selectivity, and i-Amylene yield to that of the non-steamed scenario for Catalyst 1. Catalyst 1 provided superior performance to that of Catalysts 2 and 3 and all other catalysts tested. Moreover, Catalyst 1 was the only catalyst providing outstanding or superior levels of performance, to maintain substantially the same performance level under steamed and non-steamed testing conditions.

Steamed Catalyst 2, consisting of about 10 percent by weight of a borosilicate molecular sieve and about 90 percent by weight alumina provided increased n-Amylene conversion over non-steamed Catalyst 2 but incurred a loss of i-Amylene selectivity, resulting in an i-Amylene yield less than that of non-steamed Catalyst 2. Catalyst 2 provided average performance under both steaming and non-steaming conditions, however, catalyst performance was adversely affected under the steaming scenario, which can closely simulate many commerical environments.

Steamed Catalyst 3, consisting of about 5 percent by weight of a borosilicate molecular sieve and about 95 percent by weight of alumina, provided increased n-Amylene conversion over non-steamed Catalyst 3 but incurred a loss of i-Amylene selectivity, resulting in an i-Amylene yield, less than that of non-steamed Catalyst 3. Catalyst 3, having a reduced amount of borosilicate molecular sieve than Catalyst 2, provided lower n-Amylene conversion but higher i-Amylene selectivity than Catalyst 2, resulting in a similar overall i-Amylene yield. Catalyst 3 provided average performance under both steaming and non-steaming conditions, however, catalyst performance was adversely affected under the steaming scenario, which can closely simulate many commercial environments.

Steamed Catalyst 4, consisting of about 5.3 percent by weight silica and about 94.7 percent by weight alumina provided reduced n-Amylene conversion and increased i-Amylene selectivity resulting in a substantially lower i-Amylene yield than in the non-steamed scenario for Catalyst 4. Catalyst 4 performance was similar to that of Catalyst 3 and inferior to that of Catalyst 1 when utilized under steamed testing conditions.

Steamed Catalyst 5, consisting of about 0.8 percent by weight fluoride and about 99.2 percent by weight alumina provided reduced n-Amylene conversion but improved i-Amylene selectivity resulting in an overall reduction in i-Amylene yield compared to the non-steamed scenario for Catalyst 5. Catalyst 5 performance was better than that of Catalysts 3 and 4 but inferior to that of Catalyst 1 when utilized under steamed testing conditions.

Steamed Catalyst 8, consisting of about 5 percent by weight of a gallosilicate molecular sieve and about 95 percent of weight of alumina provided reduced n-Amylene conversion and increased i-Amylene selectivity resulting in an overall increase in i-Amylene yield compared to the non-steamed scenario for Catalyst 8. Catalyst 8 performance was similar to that of Catalyst 3 and 4 and inferior to that of Catalysts 1 and 5 when utilized under steamed testing conditions.

Steamed Catalyst 9, consisting of about 5 percent by weight of beta zeolite and about 95 percent by weight of alumina provided similar n-Amylene conversion, i-Amylene selectivity, and i-Amylene yield compared to the non-steamed scenario for Catalyst 9. However, Catalyst 9 performance was inferior to that of Catalysts 1-5 and only slightly better than that of Catalyst 8, when utilized under steamed testing conditions.

Steamed Catalyst 10, consisting of about 5 percent by weight of ZSM-5 silicalite and about 95 percent by weight of alumina also provided similar n-Amylene conversion, i-Amylene selectivity, and i-Amylene yield compared to the non-steamed scenario for Catalyst 10. However, Catalyst 10 performance was also inferior to that of Catalysts 1-5 and only slightly better than that of Catalysts 8 and 9 when utilized under steamed testing conditions.

EXAMPLE 14

Catalyst 1, consisting of about 10.0 percent by weight of a borosilicate molecular sieve and about 90 percent by weight of silica, was tested in a manner similar to that described in Example 12 over varying feed space velocities of 4, 10, 16, 20, and 32 WHSV (hr$^{-1}$). The catalyst composition, process conditions, and product yields, conversions, and selectivities for these tests are provided in Table 5.

TABLE 5

| | CATALYST | | | | |
|---|---|---|---|---|---|
| | 10% HAMS/ 90% SILICA | 10% HAMS/ 90% SILICA | 10% HAMS/ 90% SILICA | 10% HAMS/ 90% ALUMINA | 10% HAMS/ 90% SILICA |
| Process Conditions | | | | | |
| Reaction Temp., F. | 700.00 | 700.00 | 700.00 | 700.00 | 700.00 |
| Pressure, atm | 1.00 | 1.00 | 1.00 | 1.00 | 1.00 |
| Feed WHSV, hr-1 | 4.00 | 10.00 | 16.00 | 20.00 | 32.00 |
| 1-Pentene WHSV, HR-1 | 2.00 | 5.00 | 8.00 | 10.00 | 16.00 |
| Product Compositions (wt. %) | | | | | |
| METHANE | 0.00 | 0.00 | 0.00 | 0.00 | 0.00 |
| ETHANE | 0.00 | 0.00 | 0.00 | 0.00 | 0.00 |
| ETHYLENE | 0.00 | 0.00 | 0.00 | 0.00 | 0.00 |
| PROPYLENE | 0.33 | 0.36 | 0.21 | 0.17 | 0.18 |
| PROPANE | 0.00 | 0.00 | 0.00 | 0.00 | 0.00 |
| ISOBUTANE | 0.01 | 0.00 | 0.00 | 0.00 | 0.00 |
| N-BUTANE | 0.00 | 0.00 | 0.00 | 0.00 | 0.00 |
| N-BUTYLENES | 1.36 | 0.94 | 0.58 | 0.59 | 0.45 |
| ISOBUTYLENE | 0.96 | 0.63 | 0.38 | 0.36 | 0.28 |
| N-PENTANE | 0.48 | 0.44 | 0.43 | 0.43 | 0.45 |
| ISOPENTANE | 50.78 | 50.63 | 50.42 | 49.49 | 50.34 |
| 1-PENTENE | 1.34 | 1.42 | 1.71 | 1.61 | 2.11 |
| TRANS-2-PENTENE | 5.44 | 5.84 | 6.78 | 6.69 | 7.91 |
| CIS-2-PENTENE | 2.74 | 2.88 | 3.37 | 3.30 | 3.95 |
| 3-M-1-BUTENE | 0.96 | 1.13 | 1.15 | 1.09 | 1.23 |
| 2-M-1-BUTENE | 8.13 | 8.74 | 8.94 | 8.79 | 8.87 |
| 2-M-2-BUTENE | 21.57 | 23.26 | 23.69 | 23.94 | 22.81 |
| C6+ | 5.90 | 3.73 | 2.34 | 3.54 | 1.42 |
| Results | 100.00 | 100.00 | 100.00 | 100.00 | 100.00 |
| n-Amylene Conv. (%) | 80.73 | 79.48 | 76.00 | 76.52 | 72.94 |
| Isoamylene Sel. (%) | 76.86 | 84.36 | 89.96 | 89.45 | 91.32 |
| Isoamylene Yld. (%) | 62.05 | 67.05 | 68.37 | 68.45 | 66.61 |

Catalyst 1 performance surprisingly improved as feed space velocity increased over the range of from about 4 WHSV (hr$^{-1}$) to about 20 WHSV (hr$^{-1}$). The best results were obtained at a feed space velocity of 20 WHSV (hr$^{-1}$), followed by results obtained at feed space velocities of 16 WHSV (hr$^{-1}$) and 10 WHSV (hr$^{-1}$) respectively. Performance rapidly declined at and above feed space velocities of 32 WHSV (hr$^{-1}$). As feed space velocity was increased until a space velocity of 20 WHSV (hr$^{-1}$) was reached, i-Amylene selectivity generally increased at a faster rate than the reduction in n-Amylene conversion, resulting in higher overall i-Amylene yield. At feed space velocities exceeding 32 WHSV (hr$^{-1}$), n-Amylene conversion declined at a faster rate then i-Amylene selectivity increased, resulting in substantially lower i-Amylene yield.

EXAMPLE 15

Catalyst 1, consisting of about 10 percent by weight of a borosilicate molecular sieve and about 90 percent by weight silica, was tested in a manner similar to that described in Example 12 over varied run lengths ranging from 1 to 10 hours in increments of 1 hour. The catalyst composition, process conditions, and product yields, conversions, and selectivities for these tests are provided in Table 6.

TABLE 6

| | CATALYST | | | | |
|---|---|---|---|---|---|
| | 2 10% HAMS/ 90% Silica | 2 10% HAMS/ 90% Silica | 2 10% HAMS/ 90% Silica | 2 10% HAMS/ 90% Silica | 2 10% HAMS/ 90% Silica |
| Process Conditions | | | | | |
| Reaction Temp., F. | 700.00 | 700.00 | 700.00 | 700.00 | 700.00 |
| Pressure, atm | 1.00 | 1.00 | 1.00 | 1.00 | 1.00 |
| Feed WHSV, hr-1 | 16.00 | 16.00 | 16.00 | 16.00 | 16.00 |
| 1-Pentene WHSV, HR-1 | 8.00 | 8.00 | 8.00 | 8.00 | 8.00 |
| Time on Tream, hrs | 1.00 | 2.00 | 3.00 | 4.00 | 5.00 |
| Product Compositions (wt. %) | | | | | |
| METHANE | 0.00 | 0.00 | 0.00 | 0.00 | 0.00 |
| ETHANE | 0.00 | 0.00 | 0.00 | 0.00 | 0.00 |
| ETHYLENE | 0.01 | 0.01 | 0.01 | 0.00 | 0.00 |
| PROPYLENE | 0.26 | 0.20 | 0.20 | 0.19 | 0.16 |
| PROPANE | 0.00 | 0.00 | 0.00 | 0.00 | 0.00 |
| ISOBUTANE | 0.01 | 0.01 | 0.01 | 0.00 | 0.00 |
| N-BUTANE | 0.00 | 0.00 | 0.00 | 0.00 | 0.00 |
| N-BUTYLENES | 0.51 | 0.45 | 0.41 | 0.42 | 0.37 |
| ISOBUTYLENE | 0.34 | 0.28 | 0.26 | 0.26 | 0.23 |
| N-PENTANE | 0.41 | 0.41 | 0.41 | 0.41 | 0.41 |
| ISOPENTANE | 49.77 | 49.59 | 49.85 | 49.49 | 49.07 |
| 1-PENTENE | 1.85 | 1.78 | 1.76 | 2.01 | 2.03 |
| TRANS-2-PENTENE | 7.41 | 7.73 | 7.76 | 8.04 | 8.25 |
| CIS-2-PENTENE | 3.67 | 3.85 | 3.84 | 3.98 | 4.09 |
| 3-M-1-BUTENE | 1.20 | 0.90 | 1.21 | 1.20 | 1.11 |

TABLE 6-continued

| CATALYST | | | | | |
|---|---|---|---|---|---|
| 2-M-1-BUTENE | 8.82 | 8.91 | 8.89 | 8.85 | 8.75 |
| 2-M-2-BUTENE | 22.94 | 23.39 | 23.03 | 22.97 | 23.12 |
| C6+ | 2.80 | 2.49 | 2.36 | 2.18 | 2.41 |
| Results | 100.00 | 100.00 | 100.00 | 100.00 | 100.00 |
| n-Amylene Conv. (%) | 73.82 | 72.96 | 72.97 | 71.61 | 70.92 |
| Isoamylene Sel. (%) | 88.71 | 90.44 | 90.23 | 93.33 | 92.38 |
| Isoamylene Yld. (%) | 65.49 | 65.98 | 65.84 | 66.83 | 65.52 |

| | 2 10% HAMS/ 90% Silica | 2 10% HAMS/ 90% Silica | 2 10% HAMS/ 90% Silica | 2 10% HAMS/ 90% Silica | 2 10% HAMS/ 90% Silica |
|---|---|---|---|---|---|
| Process Conditions | | | | | |
| Reaction Temp., F. | 700.00 | 700.00 | 700.00 | 700.00 | 700.00 |
| Pressure, atm | 1.00 | 1.00 | 1.00 | 1.00 | 1.00 |
| Feed WHSV, hr-1 | 16.00 | 16.00 | 16.00 | 16.00 | 16.00 |
| 1-Pentene WHSV, HR-1 | 8.00 | 8.00 | 8.00 | 8.00 | 8.00 |
| Time on Tream, hrs | 6.00 | 7.00 | 8.00 | 9.00 | 10.00 |
| Product Compositions (wt. %) | | | | | |
| METHANE | 0.00 | 0.00 | 0.00 | 0.00 | 0.00 |
| ETHANE | 0.00 | 0.00 | 0.00 | 0.00 | 0.00 |
| ETHYLENE | 0.01 | 0.00 | 0.01 | 0.00 | 0.00 |
| PROPYLENE | 0.19 | 0.12 | 0.16 | 0.15 | 0.15 |
| PROPANE | 0.00 | 0.00 | 0.00 | 0.00 | 0.00 |
| ISOBUTANE | 0.00 | 0.00 | 0.00 | 0.00 | 0.00 |
| N-BUTANE | 0.00 | 0.00 | 0.00 | 0.00 | 0.00 |
| N-BUTYLENES | 0.41 | 0.30 | 0.33 | 0.31 | 0.33 |
| ISOBUTYLENE | 0.24 | 0.19 | 0.20 | 0.19 | 0.18 |
| N-PENTANE | 0.40 | 0.40 | 0.40 | 0.40 | 0.40 |
| ISOPENTANE | 49.89 | 48.93 | 49.60 | 49.52 | 49.37 |
| 1-PENTENE | 2.08 | 2.06 | 1.94 | 2.14 | 2.18 |
| TRANS-2-PENTENE | 8.36 | 8.43 | 8.55 | 8.67 | 8.87 |
| CIS-2-PENTENE | 4.09 | 4.17 | 4.23 | 4.27 | 4.36 |
| 3-M-1-BUTENE | 1.03 | 1.14 | 1.18 | 1.08 | 1.12 |
| 2-M-1-BUTENE | 8.73 | 8.65 | 8.67 | 8.59 | 8.41 |
| 2-M-2-BUTENE | 22.73 | 22.98 | 22.77 | 22.54 | 22.24 |
| C6+ | 1.84 | 2.63 | 1.96 | 2.14 | 2.39 |
| Results | 100.00 | 100.00 | 100.00 | 100.00 | 100.00 |
| n-Amylene Conv. (%) | 70.59 | 70.32 | 70.21 | 69.47 | 68.82 |
| Isoamylene Sel. (%) | 91.43 | 92.57 | 92.31 | 92.08 | 91.65 |
| Isoamylene Yld. (%) | 64.54 | 65.10 | 64.81 | 63.97 | 63.07 |

Catalyst 2 performance remained steady over the duration of the tests. Over the 10 hour run length, n-Amylene conversion dropped slightly while i-Amylene selectivity increased slightly. These results affirm that the catalyst of the present invention is resistant to catalyst deactivation attendant to other catalysts used in the prior art.

Other embodiments of the invention will be apparent to those skilled in the art from a consideration of this specification or from practice of the invention disclosed herein. It is intended that this specification be considered as exemplary only with the true scope and spirit of the invention being indicated by the following claims.

That which is claimed is:

1. A process for isomerizing an olefinic hydrocarbon feedstock and producing an olefinic isomerate product, wherein said feedstock comprises at least 10 weight percent of an olefinic hydrocarbon having 5 carbon atoms, comprising contacting said feedstock at isomerization conditions with an isomerization catalyst, said isomerization catalyst comprising from about 0.01 weight percent to less than 50 weight percent borosilicate and from about 20 weight percent to about 99.99 weight percent of silica.

2. The process of claim 1 wherein said catalyst is periodically regenerated.

3. The process of claim 1 wherein said isomerization conditions comprise a reaction temperature of from about 500° F. to about 1000° F., a reaction pressure of from about 0 psig to about 200 psig, and a feedstock weight hourly space velocity of from about 4 hr$^{-1}$ to about 32 hr$^{-1}$.

4. The process of claim 1 wherein said catalyst comprises from about 0.01 weight percent to about 30 weight precent borosilicate and from about 20 weight percent to about 30 weigth percent of silica, and said borosilicate is HAMS-1B-3.

5. The process of claim 1 wherein a substantial portion of said contacting step takes place in at least one moving column reactor.

6. The process of claim 1 wherein a substantial portion of said contacting step takes place in a fluidized bed reactor.

7. The process of claim 1 wherein said contacting step takes place in a reaction zone comprising at least one fixed bed reactor comprising said isomerization catalyst and wherein a substantial portion of said catalyst in at least one of said reactors is regenerated at least once every 400 hours.

8. The process of claim 7 wherein said catalyst is utilized in at least one fixed bed reactor, said feedstock comprises at least 50 weight percent olefinic hydrocarbon having 5 carbon atoms, and said i-Amylene yield is at least 60 percent.

9. The process of claim 1 wherein said feedstock weight hourly space velocity ranges from about 10 hr$^{-1}$ to about 32 hr$^{-1}$.

10. The process of claim 7 wherein said reaction zone comprises the presence of hydrogen, wherein said hydrogen is present with said feedstock at an average hydrogen to feedstock ratio of about 200 standard cubic feed per barrel to about 10000 standard cubic feet per barrel.

11. A process for isomerizing an olefinic hydrocarbon feedstock and producing an olefinic isomerate product, wherein said feedstock comprises at least 25 weight percent of an olefinic hydrocarbon having 5 carbon atoms, comprising contacting said feedstock at isomerization conditions comprising a reaction temperature ranging from about 500° F. to about 1000° F., a reaction pressure ranging from about 0 psig to about 200 psig, and a feedstock weight hourly space velocity ranging from about 4 $hr^{-1}$ to about 32 $hr^{-1}$, with an isomerization catalyst, said isomerization catalyst comprising from about 0.01 weight percent to about 30 weight percent borosilicate and from about 20 weight percent to about 99.99 weight percent of silica.

12. The process of claim 11 wherein said catalyst comprises from about 0.01 weight percent to about 15 weight percent of borosilicate and from about 50 weight percent to about 99.99 weight percent silica and said borosilicate is HAMS-1B-3.

13. The process of claim 11 wherein said contacting step takes place in a reaction zone comprising at least one fixed bed reactor comprising said isomerization catalyst and wherein a substantial portion of said catalyst in at least one of said reactors is regenerated at least once every 400 hours.

14. The process of claim 13 wherein said feedstock weight hourly space velocity ranges from about 10 $hr^{-1}$ to about 32 $hr^{-1}$.

15. The process of claim 11 wherein at least a portion of said feedstock has been processed prior to said isomerization in at least one process selected from the group consisting of a amyl tertiary methyl ether process, fluid catalytic cracking process, coking process, methyl tertiary butyl ether process, and a dehydrogenation process.

16. The process of claim 11 wherein said olefinic isomerate product comprises i-Amylene and n-Amylene, said olefinic isomerate product is directed to isomer separation means, said i-Amylene is substantially separated from said n-Amylene, and said n-Amylene is recycled back to said contacting step.

17. The process of claim 16 wherein said isomer separation means is at least one member selected from the group consisting of a distillation tower and a molecular sieve.

18. The process of claim 16 wherein said substantially separated i-Amylene is directed to an amyl tertiary methyl ether process.

19. The process of claim 11 wherein said reaction zone comprises the presence of hydrogen, wherein said hydrogen is present with said feedstock at an average hydrogen to feedstock ratio of about 200 standard cubic feet per barrel to about 10000 standard cubic feet per barrel.

* * * * *